(12) United States Patent
Kahn et al.

(10) Patent No.: US 7,259,280 B1
(45) Date of Patent: Aug. 21, 2007

(54) PROCESS FOR PRODUCING ALKENYL ALCOHOLS

(75) Inventors: Andrew P. Kahn, Eagleville, PA (US); Stephen H. Harris, Kennett Square, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 37 days.

(21) Appl. No.: 11/386,131

(22) Filed: Mar. 22, 2006

(51) Int. Cl.
*C07C 29/60* (2006.01)
(52) U.S. Cl. .................................................. 568/903
(58) Field of Classification Search ................ 568/903
See application file for complete search history.

(56) References Cited

U.S. PATENT DOCUMENTS 4,490,567 A * 12/1984 Drake ..................... 585/324

OTHER PUBLICATIONS

N. Nagato, "Allyl Alcohol and Monoallyl Derivatives" in *Kirk-Othmer Encyclopedia of Chemical Technology* (2004) 1, John Wiley & Sons, Inc. On-line Edition.
S. Sato et al., *Catal. Commun*, 4 (2003) 77.
S. Sato et al., *J. Mol. Catal. A: Chem. 221* (2004) 177.
A. Stiles, "Getting the Catalyst and the Support Together" in *Catalyst Supports and Supported Catalysts* (1987) 1.
S. Sato et al., *J. Catal. 178* (1998) 264.

* cited by examiner

*Primary Examiner*—Elvis O. Price
(74) *Attorney, Agent, or Firm*—Yuanzhang Han

(57) ABSTRACT

A process for producing an alkenyl alcohol from a diol is disclosed. The process comprises dehydrating a diol in the presence of a catalyst comprising cerium oxide supported on a carrier. The carrier has a surface area in the range of 0.1 to 50 $m^2/g$. The catalyst is more active than unsupported cerium oxide.

20 Claims, No Drawings

PROCESS FOR PRODUCING ALKENYL ALCOHOLS

FIELD OF THE INVENTION

The invention relates to a process for producing an alkenyl alcohol from a diol.

BACKGROUND OF THE INVENTION

Alkenyl alcohols are useful chemical intermediates due to their dual functionalities (a carbon-carbon double bond and a hydroxy group). Allyl alcohol (AA), the simplest alkenyl alcohol, is used in synthesizing epichlorohydrin, 1,4-butanediol, styrene-allyl alcohol copolymers, and diethylene glycol bis(allyl carbonate), a monomer for plastic optical lens (N. Nagato, "Allyl Alcohol and Monoallyl Derivatives," in *Kirk-Othmer Encyclopedia of Chemical Technology* (2005) John Wiley & Sons, Inc., On-line Edition, posted on Feb. 13, 2004).

Allyl alcohol is commercially produced by two processes: isomerization of propylene oxide, and acetoxylation of propylene followed by hydrolysis of allyl acetate. Other methods investigated for allyl alcohol production include allyl chloride hydrolysis and propylene oxidation to acrolein followed by the reduction of acrolein (N. Nagato, supra). Recently, R. Sato et al. reported a process for making alkenyl alcohols by dehydrating diols in the presence of cerium oxide or a cerium-containing mixed oxide (*Catal. Commun.* 4(2) (2003) 77; *J. Mol. Catal. A: Chem.* 221(1-2) (2004) 177). Specifically, allyl alcohol is produced from 1,3-propanediol (PDO). However, improvement of the catalyst is needed to make the process commercially viable.

SUMMARY OF THE INVENTION

The invention relates to a process for producing an alkenyl alcohol from a diol. The process comprises dehydrating a diol in the presence of a catalyst comprising cerium oxide supported on a carrier. The carrier has a surface area in the range of 0.1 to 50 $m^2/g$. The catalyst is more active than unsupported cerium oxide.

DETAILED DESCRIPTION OF THE INVENTION

The process of the present invention comprises dehydrating a diol. The diol is an organic compound containing two hydroxy groups that are separated by at least three carbons. In addition, the diol contains at least one beta-hydrogen relative to one of the hydroxy groups. The diol may have other functionalities including, e.g., ketone, aldehyde, ester, halide, ether, and the like. Suitable diols include 1,3-propanediol, 2-methyl-1,3-propanediol, 1,3-butanediol, 1,4-butanediol, 2-phenyl-1,3-propanediol, and 1,6-hexanediol. The preferred diol is a 1,3-diol. A 1,3-diol is an organic compound containing two hydroxy groups that are separated by three carbons (e.g., 1,3-propanediol, 2-methyl-1,3-propanediol, 1,3-butanediol, 1,3-hexanediol, 2-phenyl-1,3-propanediol). Preferably, the 1,3-diol is 1,3-propanediol or 2-methyl-1,3-propanediol. More preferably, the 1,3-diol is 1,3-propanediol.

The process comprises a dehydration reaction in which the diol loses a water molecule to form an alkenyl alcohol. The alkenyl alcohol contains at least one carbon-carbon double bond (C=C) and at least one hydroxy (—OH) group. The simplest alkenyl alcohol is allyl alcohol. Other examples include 2-methyl-2-propen-1-ol, 2-buten-1-ol, 3-buten-2-ol, 2-phenyl-2-propen-1-ol, 3-buten-1-ol, and the like. Preferably, the alkenyl alcohol is allyl alcohol or 2-methyl-2-propen-1-ol. Most preferably, the alkenyl alcohol is allyl alcohol.

The process is performed in the presence of a catalyst comprising a carrier (support). Catalyst carriers are well known in the art (see, A. B. Stiles, "Getting the Catalyst and the Support Together," in *Catalyst Supports and Supported Catalysts* (1987) Butterworths Publishers, pp. 1-10). Suitable carriers include alumina, silica, titania, zirconia, magnesia, calcium oxide, calcium carbonate, magnesium carbonate, silica-alumina, silica-titania, silica-zirconia, carbon, and the like, and mixtures thereof. Inorganic carriers are preferred. More preferably, the carrier is an alumina. Alpha-alumina is particularly preferred.

The carrier has a surface area in the range of 0.1 to 50 square meters per gram ($m^2/g$) based on the BET method. Preferably, the carrier surface area is from 0.5 to 30 $m^2/g$, more preferably from 1 to 10 $m^2/g$. The carrier generally has an average particle size of at least 0.1 micrometer ($\mu m$) in diameter, preferably at least 1 $\mu m$, most preferably, at least 10 $\mu m$.

The catalyst comprises cerium oxide. The content of cerium in the catalyst is typically in the range of 2 to 80 weight percent (wt. %), preferably in the range of 5 to 60 wt. %, more preferably in the range of 10 to 40 wt. % relative to the catalyst.

Many cerium compounds or complexes may be used as the cerium source for preparing the catalyst. They include cerium oxides, hydroxides, nitrates, sulfates, halides, and carboxylates, and mixtures thereof. Examples of suitable sources of cerium include cerium(IV) oxide, cerium(IV) hydroxide, cerium(IV) nitrate, cerium(IV) sulfate, cerium (IV) perchlorate, cerium(IV) acetate, cerium(IV) fluoride, cerium(III) acetate, cerium(III) acetylacetonate, cerium(III) bromide, cerium(III) carbonate, cerium(III) chloride, cerium (III) fluoride. The cerium source is converted to cerium oxide before the catalyst is used for the dehydration reaction.

There are many suitable methods for preparing the catalyst. A cerium compound may be supported on the carrier by impregnation, ion exchange, adsorption, precipitation, or the like. It may be supported on the carrier in a single step or in multiple steps. A solution containing a cerium compound may be used. Suitable solvents for cerium compounds include water, alcohols, ketones, carboxylic acids, nitriles, amides, and the like, and mixtures thereof. Examples of suitable solvents are water, methanol, ethanol, isopropanol, acetone, acetonitrile, N,N-dimethylformamide, acetic acid, and citric acid. A mixture containing cerium oxide nanoparticles dispersed in water or other solvents (available from Aldrich) can also be used. It may be necessary to calcine the impregnated carrier to form the desired catalyst. Suitable calcination temperatures range from 300° C. to 900° C., preferably from 400° C. to 600° C. When it is desirable to burn off organic residues from the impregnated carrier, the calcination can be carried out in an oxygen-containing atmosphere.

To further improve the catalyst activity and/or selectivity, it may be advantageous to include a metal oxide in the catalyst. Suitable metals of the metal oxide include aluminum, magnesium, calcium, barium, iron, cobalt, nickel, titanium, vanadium, scandium, yttrium, and the like, and mixtures thereof. Cerium oxide and the metal oxide if used are generally well mixed in the catalyst; the mixture is called a "mixed oxide." Typically, the catalyst contains particles of cerium oxide and/or the metal oxide that are smaller than 100 nanometer (nm) in diameter. Preferably, they are smaller than 10 nm. Cerium oxide and the metal oxide may be intimately mixed at the atomic level to form a solid solution. The content of the metal is typically in the range of 0.5 to 40 wt. %, preferably in the range of 1 to 30 wt. %, more preferably in the range of 2 to 20 wt. % relative to the catalyst.

Many metal compounds or complexes may be used as sources of the metal oxide. They include metal oxides, hydroxides, nitrates, sulfates, halides, and carboxylates, and mixtures thereof. A mixture containing mixed metal oxide nanoparticles dispersed in water (see 2005-2006 Aldrich catalog, pp. 590-591) or other solvents can also be used. For example, a molten mixture obtained by mixing cerium(III) nitrate, magnesium nitrate, and citric acid (see *J. Catal.* 178 (1998) 264) can be used to impregnate a carrier. The metal source may be supported on the carrier by impregnation, ion exchange, adsorption, and the like. The cerium source and the metal source may be supported in a single step or in separate steps.

The process of the invention is performed at a temperature effective in dehydrating a diol to an alkenyl alcohol, preferably from 250° C. to 450° C., more preferably from 300° C. to 400° C., and most preferably from 325° C. to 375° C. The diol may be a liquid or a gas under the reaction conditions. Preferably, the diol is a gas under the reaction conditions. Although the pressure is not critical, it may be advantageous to operate the process at a total pressure of 0.5 to 1.5 atmospheres.

The process may be performed in a continuous flow, semi-batch, or batch mode. Preferably, it is performed in a continuous flow mode. The catalyst may be in a slurry, a fluidized bed, or a fixed bed. Preferably, it is in a fixed bed. The amount of catalyst used relative to the diol is not critical. In a continuous flow reaction, the weight hourly space velocity, WHSV (grams of diol fed per gram of catalyst per hour) is typically in the range of 0.5 to 200 g/g cat/h. Preferably, WHSV is in the range of 1 to 20 g/g cat/h. In a batch reaction, the weight ratio of the diol to the catalyst is generally from 1:1 to 1000:1, preferably from 5:1 to 100:1.

An inert gas may be used in the process. Inert gases dilute the feed and may help to improve catalyst performance. Suitable inert gases are helium, argon, nitrogen, methane, ethane, propane, water, and carbon dioxide, and mixtures thereof. Because it is cheap and readily available, nitrogen is preferred. The molar ratio of the inert gas to the diol is typically from 1 to 100, preferably from 2 to 50, more preferably from 3 to 20.

The following examples merely illustrate the invention. Those skilled in the art will recognize many variations that are within the spirit of the invention and scope of the claims.

EXAMPLE 1

Cerium Oxide Catalyst

Cerium nitrate hexahydrate (17.8 g) and citric acid (5 g) are ground to a powder and placed in a crucible. Water is added with mixing to form a paste. The paste is heated in an oven at 95° C. for 2 h, then at 170° C. for 2 h. The dried solid is crushed and calcined in air at 500° C. for 2 h. Cerium oxide catalyst (Catalyst A) is obtained.

EXAMPLE 2

Cerium Oxide-on-Alumina Catalyst

Gamma-alumina (Porocel Dynocel, particle size=0.6-1.4 mm, surface area=270 $m^2/g$) is dried at 110° C. for 2 h. A cerium nitrate solution is prepared by mixing cerium nitrate hexahydrate (17 g) and citric acid (5 g). A portion of the solution (10 g) and water (17 g) is added to the dried alumina (10 g). The impregnated alumina is dried at 110° C. for 1 h. Additional cerium nitrate solution (5 g) is added to the above solid, which is then dried at 110° C. for 1 h, at 170° C. for 2 h, and finally calcined in air at 500° C. for 2 h. The solid obtained (Catalyst B, 12.0 g) contains 16 wt. % Ce and has a surface area of 170 $m^2/g$.

EXAMPLE 3

Cerium Oxide-on-Alumina Catalyst

Alpha-alumina (Engelhard, particle size=0.6-1.4 mm, surface area=4 $m^2/g$, 17.8 g) is dried at 110° C. for 1 h, cooled to room temperature, then mixed with an aqueous cerium nitrate solution (50 wt. %, 11.8 g). The solid is dried at 95° C. for 2 h. It is then mixed with more cerium nitrate solution (50 wt. %, 8.5 g). The solid is dried at 95° C. for 2 h, at 170° C. for 2 h, and then calcined at 500° C. in air for 2 h. The solid obtained (Catalyst C) contains 12 wt. % Ce and has a surface area of 24 $m^2/g$.

EXAMPLE 4

Cerium Oxide-on-Alumina Catalyst

Alpha-alumina (Engelhard, particle size=0.6-1.4 mm, surface area=4 $m^2/g$, 17.8 g) is dried at 110° C. for 1 h, cooled to room temperature, then mixed with an aqueous cerium nitrate solution (50 wt. %, 9.5 g). The impregnated solid is dried at 110° C. for 1 h, at 170° C. for 2 h, and then calcined at 500° C. in air for 2 h. The solid obtained (Catalyst D) contains 6.6 wt. % Ce and has a surface area of 12 $m^2/g$.

EXAMPLE 5

PDO Dehydration to Allyl Alcohol

A tubular reactor (0.97" ID, 316 SS) is equipped with a 0.25" OD thermowell running down the center of the tube.

Catalyst C (particle size=0.6-1.4 mm) is charged to the reactor. The catalyst bed is placed between two plugs of quartz wool. The reactor is heated to 350° C. with a sand bath. 1,3-Propanediol (PDO, 11.37 g/h) and nitrogen (20 standard liters per hour) are fed to the top of the reactor. The test continues for 79 h. Samples are collected hourly and analyzed by gas chromatography (GC). Results are shown in Table 1. In addition to allyl alcohol (AA), minor amounts of methanol, ethanol, n-propanol, acrolein, and propionaldehyde are also detected. The weight hourly space velocity relative to the catalyst, WHSV (g PDO/g cat/h), is the grams of PDO fed per gram of catalyst per hour. The weight hourly space velocity relative to cerium, WHSV (g PDO/g Ce/h), is the grams of PDO fed per gram of cerium contained in the catalyst per hour. The catalyst activity (g AA/g Ce/h) is the moles of AA formed per gram of Ce per hour. Selectivity to AA (%) is the moles of AA formed per mole of PDO consumed. Similarly, selectivity to methanol is the moles of methanol formed per mole of PDO consumed.

EXAMPLE 6

PDO Dehydration to Allyl Alcohol

The procedure of Example 5 is repeated, except that Catalyst D is used.

COMPARATIVE EXAMPLES 7-10

PDO Dehydration to Allyl Alcohol

The procedure of Example 5 is repeated with catalysts shown in Table 1.

Table 1 shows that a catalyst containing cerium oxide supported on a low surface area alumina gives much higher activity than unsupported cerium oxide (comparing Examples 5 and 6 with C7). Supporting cerium oxide on a high surface area alumina has little effect on the catalyst activity (comparing Examples C7 and C8). However, it lowers the selectivity to AA from 80% to 70%. High surface area alumina itself shows significant activity in decomposing PDO (52% conversion in Example C10), but with very low selectivity to the desired product, AA (18% selectivity).

TABLE 1

Production of Allyl Alcohol from 1,3-Propanediol

| Example | 5 | 6 | C7 | C8 | C9 | C10 |
|---|---|---|---|---|---|---|
| Catalyst | C | D | A | B | α-Al$_2$O$_3$[1] | γ-Al$_2$O$_3$[2] |
| Support | α-Al$_2$O$_3$ | α-Al$_2$O$_3$ | — | γ-Al$_2$O$_3$ | — | — |
| Support Surface Area (m$^2$/g) | 4 | 4 | — | 270 | — | — |
| WHSV (g PDO/g cat/h) | 4.0 | 4.0 | 22.3 | 4.7 | 4.5 | 2.6 |
| WHSV (g PDO/g Ce/h) | 33.7 | 61.3 | 27 | 29 | — | — |
| PDO Conversion (%) | 82 | 60 | 65 | 60 | <1 | 52 |
| Activity (g AA/g Ce/h) | 16 | 20 | 11 | 10 | — | — |
| Selectivity to MeOH (%) | 3.5 | 4 | 1 | 7.5 | 7 | 50 |
| Selectivity to AA (%) | 75 | 75 | 80 | 70 | 5 | 18 |

[1]Obtained from Engelhard, surface area = 4 m$^2$/g.
[2]Obtained form Porocel Dynocel, surface area = 270 m$^2$/g.

We claim:

1. A process for producing an alkenyl alcohol, which comprises dehydrating a diol in the presence of a catalyst comprising cerium oxide supported on a carrier, wherein the carrier has a surface area in the range of 0.1 to 50 m$^2$/g.

2. The process of claim 1 wherein the catalyst further comprises a metal oxide.

3. The process of claim 2 wherein the metal oxide is selected from the group consisting of oxides of aluminum, magnesium, calcium, barium, iron, cobalt, nickel, titanium, vanadium, scandium, yttrium, and mixtures thereof.

4. The process of claim 1 wherein the carrier is selected from the group consisting of alumina, silica, titania, zirconia, magnesia, calcium oxide, calcium carbonate, magnesium carbonate, silica-alumina, silica-titania, silica-zirconia, carbon, and mixtures thereof.

5. The process of claim 1 wherein the carrier is an alumina.

6. The process of claim 1 wherein the carrier is an alpha-alumina.

7. The process of claim 1 wherein the carrier has a surface area in the range of 1 to 10 m$^2$/g.

8. The process of claim 1 performed at a temperature in the range of 250 to 450° C.

9. The process of claim 1 performed at a temperature in the range of 300 to 400° C.

10. The process of claim 1 performed in the presence of an inert gas.

11. The process of claim 1 performed in a continuous flow mode.

12. The process of claim 1 wherein the catalyst is in a fixed bed.

13. The process of claim 1 performed at a pressure of 0.5 to 1.5 atmospheres.

14. The process of claim 1 wherein the diol is a gas under the reaction conditions.

15. The process of claim 1 wherein the diol is a 1,3-diol.

16. The process of claim 1 wherein the diol is 1,3-propanediol and the alkenyl alcohol is allyl alcohol.

17. The process of claim 1 wherein the diol is 2-methyl-1,3-propanediol and the alkenyl alcohol is 2-methyl-2-propen-1-ol.

18. A process for producing allyl alcohol, which comprises dehydrating 1,3-propanediol in the presence of a catalyst comprising cerium oxide supported on a carrier, wherein the carrier has a surface area in the range of 0.1 to 50 m$^2$/g.

19. The process of claim 18 wherein the catalyst is in a fixed bed.

20. The process of claim 18 wherein the carrier is an alumina.

* * * * *